United States Patent [19]

Anderson

[11] Patent Number: 6,107,516
[45] Date of Patent: Aug. 22, 2000

[54] PRODUCTION OF AROMATIC HYDROXYCARBOXYLIC ACIDS

[75] Inventor: Arthur William Anderson, Wilmington, Del.

[73] Assignee: E. I. du Pont de Nemours and Company, Wilmington, Del.

[21] Appl. No.: 09/180,845

[22] PCT Filed: May 14, 1997

[86] PCT No.: PCT/US97/08173

§ 371 Date: Nov. 17, 1998

§ 102(e) Date: Nov. 17, 1998

[87] PCT Pub. No.: WO97/44305

PCT Pub. Date: Nov. 27, 1997

Related U.S. Application Data

[60] Provisional application No. 60/017,987, May 20, 1996.

[51] Int. Cl.[7] .................................................... C07C 51/15
[52] U.S. Cl. ............................................ 562/424; 562/423
[58] Field of Search ....................... 562/424, 423

[56] References Cited

U.S. PATENT DOCUMENTS

| | | | |
|---|---|---|---|
| 3,595,907 | 7/1971 | Patmore et al. | 562/423 |
| 3,825,593 | 7/1974 | Meek | 562/424 |
| 4,032,555 | 6/1977 | Bottaccio et al. | 558/406 |
| 4,730,083 | 3/1988 | Pastor et al. | 562/423 |
| 4,820,868 | 4/1989 | Mitamura et al. | 562/482 |

OTHER PUBLICATIONS

Troupel et al ,electrosynthesis of aryl carbonates from aryl halides and carbon dioxide catalyzed lby organonickel complexes, Nouv. J. Chim.; 5(12); p. 621–5, Jan. 1981.

*Primary Examiner*—Paul J. Killos
*Assistant Examiner*—Taylor Victor Oh

[57] ABSTRACT

A process for the production of aromatic hydroxycarboxylic acids such as salicylic acid comprising contacting an aromatic hydroxy compound such as phenol with carbon dioxide in the presence of fluoride ion. The products are useful as pharmaceuticals and chemical intermediates, and as monomers for polymers.

19 Claims, No Drawings

PRODUCTION OF AROMATIC HYDROXYCARBOXYLIC ACIDS

This application is an International 371 of PCT/US97/08173 filed May 14, 1997, also claims benefit of Provisional Application No. 60/017,987 filed May 20, 1996.

FIELD OF THE INVENTION

This invention concerns a process for the production of aromatic hydroxycarboxylic acids by contacting an aromatic hydroxy compound and carbon dioxide in the presence of fluoride ion.

TECHNICAL BACKGROUND

Aromatic hydroxy acids are important items of commerce. For instance o-hydroxybenzoic acid (salicylic acid) is used as a chemical intermediate, for instance to make aspirin, while p-hydroxybenzoic acid is used to make parabens and is also used as a monomer in making polyesters. Aromatic hydroxy acids can be manufactured using the Kolbe-Schmitt reaction, which is a reaction of an alkali metal salt of an aromatic hydroxy compound with carbon dioxide, usually under elevated temperature and pressure. The Kolbe-Schmitt reaction has been a standard procedure for the preparation of aromatic hydroxy acids for over 100 years, see for instance A. S. Lindsey, et al., Chem. Rev., vol. 57, p. 583–620 (1957). However, this process is complex and difficult to run, involving several manufacturing steps, which adds to the cost of the final product. Also, substantial cost is incurred for the use of corrosive compounds such as NaOH or KOH which are subsequently discarded (as sodium or potassium salts).

SUMMARY OF THE INVENTION

This invention concerns a process for the production of aromatic hydroxycarboxylic acids, comprising contacting, at a temperature of about 100° C. to about 300° C., an aromatic hydroxy compound and carbon dioxide, in the presence of fluoride ion, wherein the carbon dioxide has a partial pressure of at least about 0.1 MPa.

DETAILS OF THE INVENTION

The product of the process is an aromatic hydroxycarboxylic acid. By an aromatic hydroxycarboxylic acid is meant a compound that contains at least one aromatic carbocyclic ring, and at least one hydroxyl group and one or more carboxyl groups (preferably one carboxyl group) attached to carbon atoms of an aromatic carbocyclic ring. This compound may contain one or more aromatic rings, and if more than one such ring is present they may be fused, as in naphthalene, connected by a covalent bond, as in biphenyl, or by a divalent group, as in diphenyl ether. There may also be inert groups attached to the aromatic ring(s), such as one or more alkyl groups. Without intending to be limited to any particular theory or explanation, it is believed that the positions in the aromatic rings which may be substituted by a carboxyl group herein are similar to those which are substituted in the Kolbe-Schmitt reaction. Therefore, at least one of these positions should preferably be unsubstituted in the aromatic hydroxy compound. Compounds which may be produced by this process include p-hydroxybenzoic acid, o-hydroxybenzoic acid, 2-hydroxy-3-methylbenzoic acid, 2-hydroxy-5-methylbenzoic acid, 2,4-dihydroxybenzoic acid, and a hydroxynapthoic acid. Preferred products are p-hydroxybenzoic acid, o-hydroxybenzoic acid, and 6-hydroxy-2-naphthoic acid.

One of the starting materials for the instant process is an aromatic hydroxy compound. By an aromatic hydroxy compound is meant a compound that contains at least one aromatic carbocyclic ring, and also contains at least one hydroxyl group attached to a carbon atom of an aromatic carbocyclic ring. This compound may contain one or more aromatic rings, and if more than one such ring is present they may be fused, as in naphthalene, connected by a covalent bond, as in biphenyl, or by a divalent group, as in diphenyl ether. There may also be inert groups attached to the aromatic ring(s), such as one or more alkyl groups. Useful aromatic hydroxy compounds include phenol, 1-naphthol, 2-naphthol, o-cresol, p-cresol, m-cresol, and resorcinol. Phenol and 2-naphthol are preferred aromatic hydroxy compounds, and phenol is especially preferred.

Another ingredient in the process is carbon dioxide. While the partial pressure of $CO_2$ in the process is not critical, it is preferred that it is at least about 0.1 MPa, more preferably in the range of about 5 MPa to about 70 MPa, and especially preferably about 10 MPa to about 25 MPa. The pressure of the $CO_2$ may also affect which positional isomer(s) of the aromatic hydroxycarboxylic acid are obtained in the process.

Fluoride ion must be present, and without intending to be limited to any particular theory it is believed to be a promoter for the instant process. It is preferred that the fluoride ion is "available" in the process. By available is meant that the fluoride ion can interact with the reactants. If the desired process proceeds, the fluoride ion is available to the reactants. Such uses of fluoride ion in organic chemistry are generally discussed in J. H. Clark, Chem. Rev., vol. 80, p. 429–451 (1980), which is hereby incorporated by reference, and the section at p. 430–431 deals with selection of fluoride ion sources. In one method the fluoride ion can be made more available by its interaction with the process medium. Certain process ingredients, such as the (solvents) polyethers triglyme or tetraglyme, tetrahydrofuran, dimethylsufoxide, acetonitrile, dimethyl ether and formals may increase the availability of the fluoride ion containing compound which is added. So-called "crown ethers" may also increase this availability. The cation associated with the fluoride anion may also affect the solubility of the fluoride in the process medium. Large monovalent cations such as cesium. rubidium and tetraalkylammonium cations may also promote the availability of the fluoride ion. Preferred fluorides are potassium fluoride, rubidium fluoride and cesium fluoride, and cesium fluoride is especially preferred. These fluorides may also be supported on an inert solid such as alumina which has been shown to markedly increase the activity of KF as described in "Michael Addition of Nitroalkane to α,β-Unsaturated Carbonyl Compounds on $KF/Al_2O_3$/PEG-4000", Chinese Chemical Letters, vol. 3, p. 159–160 (1992).

The ratio of aromatic hydroxy compound to $CO_2$ is not critical. It is preferred that the ratio of fluoride:aromatic hydroxy compound is about one or more, more preferably about 2 or more, and especially preferably about 4 or more. A preferred upper limit on the ratio of crystalline fluorides:aromatic hydroxy compound is about 10, more preferably about 6. It is believed that because the availability of fluoride ion as a catalyst for the reaction will depend on the surface area when in the solid state, the ratio of fluoride to reactants can be very low if the fluoride is dispersed on a solid surface such as alumina, or if the fluoride has a high specific surface area.

The process of the present invention is advantageously carried out at a temperature of about 100° C. to about 300°

C. A preferred temperature range for the process is about 110° C. to about 250° C. When phenol is used as the aromatic hydroxy compound, a preferred temperature range is about 110° C., to about 160° C. As is well known in the Kolbe-Schmitt reaction, the temperature of the process may affect which isomer(s) of the aromatic hydroxy acid is (are) obtained. It is believed that the instant process may also be affected, and that the artisan would be able to optimize the process temperature (and other reaction conditions) to obtain a particular aromatic hydroxy acid isomer with minimal routine experimentation.

It is also preferred that there is some agitation or other movement of the process ingredients to ensure mixing of these ingredients. A dispersant (a material which is liquid at the process temperature, and which may or may not be a solvent for any or all of the starting materials and/or products) may optionally be used in the process. The dispersant should not interfere with (stop) the process. Useful dispersants include hydrocarbons such as hexadecane, crown ether, and (poly)ethers such as triglyme and tetraglyme. It is also preferred that less than 10 mole percent (based on the amount of aromatic hydroxy compound originally present) of strong bases such as KOH or NaOH are present, and more preferred if they are essentially absent.

The process may be run for a period of time sufficient to produce the desired product. This will typically be in the range of about 1 min. to several days, depending on process conditions. Which positional isomer(s) of the aromatic hydroxycarboxylic acid are obtained may depend on how long the process is allowed to proceed. During the process an initially formed aromatic hydroxycarboxylic acid may be (partially) isomerized to another compound which is a positional isomer of the originally formed product. Optimum times (and other process conditions) for producing any particular isomer may be determined by minimal experimentation.

The aromatic hydroxycarboxylic acids may be isolated by methods well known to the artisan. For instance, if the product is a solid, it may precipitate from the reaction mixture especially upon cooling, and be isolated by filtration. See the Examples for methods of isolation.

It is preferred that the process be carried out under conditions that are as anhydrous as can be practically and economically obtained. The presence of significant amounts of water reduces the yield of the desired product(s). Oxygen should also be excluded to the extent practicable, because of the propensity of organic compounds, especially phenols, to be oxidized at higher temperatures.

In the Examples, the following abbreviations are used:

N—2-naphthol

PHBA—p-hydroxybenzoic acid

SA—salicylic acid (o-hydroxybenzoic acid)

Ratios of fluorides to substrates (e.g., phenol) are in moles.

In the Examples various types of equipment are used. These are given an identifying number which is shown in Table 1.

TABLE 1

Key for Experimental Equipment

| 1 | Heating Tape |
| 2 | Sandbath |
| 3 | Shaker Tubes |
| 4 | Titanium |

Table 2 gives the characteristics of each type of equipment. The equipment is compared in terms of agitation, volume, temperature control, pressure rating, and material of construction. Each of the methods used with this equipment is described below.

TABLE 2

| | Experimental Equipment | | | |
| --- | --- | --- | --- | --- |
| | Heating Tape | Sand Bath | Shaker Tube | Titanium Reactor |
| Agitation | None | None | Horizontal motion with stainless steel balls in reactor | Mechanical stirring with baffles |
| Volume | 10–15 ml | 5 ml | approx. 5 ml | approx. 100 ml |
| Reactor Material of Construction | 316 Stainless Steel | 316 Stainless Steel | 316 Stainless Steel | Titanium |
| Temperature Probe | Outside | Outside | Outside | Inside |
| Temperature Control | Heating tape and insulation | Immersed in sand | Enclosed in aluminum block and insulated | Jacket for heat transfer fluid and insulation |
| Pressure Rating | 69 MPa | 69 MPa | 69 MPa | 12 MPa |

1. Heating Tape Method

The heating tape equipment is a preliminary experimental setup consisting of a 10–15 ml high pressure tube reactor made of stainless steel, a pressure gauge, and inlet and outlet valves. The reactor was heated by heating tape that is wrapped around the reactor, and the temperature was measured on the outside of the reactor beneath the heating tape. The temperature probe was connected to a temperature controller, which was used in conjunction with a Variac connected to the heating tape, to maintain the desired temperature of the reactor.

Starting material was weighed and added to the reactor in the glove box. The reactor was then pressurized with carbon dioxide using a pump to reach an estimated pressure that would give a final pressure after heating the reactor that is less than the equipment limitations. Next, the reactor was wrapped with heating tape and a temperature probe was place between the tape and the outside of the reactor. All equipment was then wrapped with insulation, so that only the pressure gauge was visible.

The reactor was heated to the desired temperature and kept there for a specified amount of time using the temperature controller and Variac. Next, the reactor was allowed to cool naturally or quenched in ice water as noted in the data tables. After the reactor cooled to room temperature, the reactor contents were depressurized slowly into a liquid solvent, either acetone or methanol, and any solids were rinsed and scraped out of the tube reactor. Analysis of the solids and liquid solvent were carried out by the indicated procedure.

2. Sandbath

The sandbath equipment is similar to the heating tape equipment except that heating is attained by a fluidized bed of sand. It is still considered as a preliminary setup because there is no agitation. This setup consists of a 5 ml high pressure tube reactor made of stainless steel, a pressure gauge, and inlet and outlet valves. A temperature controller was part of the fluidized sand bath and was used to maintain the desired temperature of the reactors. The volume of the tube reactor is smaller than the reactors used in the heating tape method because of the size and geometry of the sandbath. The larger volume (10–15 ml) reactors could only be oriented vertically in the sandbath which caused the starting material to form a plug in one end of the reactor. Smaller volume reactors could be positioned horizontally to prevent this solid plug from forming.

Starting material was weighed and added to the reactors in the glove box. The reactors were then pressurized with carbon dioxide using a pump to reach an estimated pressure that would give a final pressure after heating the reactors that is less than the equipment limitations. The reactors and pressure gauge were placed on a holder so that only the pressure gauge was visible above the sand. The reactor was heated to the desired temperature and maintained at this temperature for a specified amount of time.

Next, the reactor was allowed to cool naturally or quenched in ice water as noted in the data tables. After the reactor cooled to room temperature, the reactor contents were depressurized slowly into a liquid solvent, either acetone or methanol, and any solids were rinsed and scraped out of the tube reactor. Analysis of the solids and liquid solvent were carried out by the indicated procedure.

3. Shaker Tubes

The shaker tube equipment consists of a temperature bath and an aluminum block with several holes for tube reactors. The tube reactors are made of stainless steel with a volume of approximately 5 ml. The aluminum block is heated by four cartridge heaters located on the top and bottom of the block. The cartridge heaters and reactor holes are spaced to get a reasonably even temperature distribution.

The temperature of the aluminum block was measured by placing a probe in a drilled hole in the top of the block. The temperature probe was connected to a temperature controller, which was used in conjunction with Variacs connected to the cartridge heaters, to maintain the desired temperature of the reactors in the block. Before starting agitation, the block was covered with insulation to decrease the amount of heat convection and to prevent anyone from touching the top of the hot aluminum block. The temperature bath was used as a mechanical source of horizontal movement and contained no water. Agitation results from horizontal movement of the temperature bath's basket containing the aluminum block at 100 rpm.

Starting material was weighed and added to the tube reactors in the glove box. Along with the starting material, ten 0.3 cm diameter stainless steel ball bearings were also added to each of the tube reactors to disperse the material during agitation. The reactors were then pressurized with carbon dioxide to an initial set point at room temperature. Next, the reactors were placed in the heating block still connected to a pressure gauge and then heated in the block to a desired temperature. The reactors were filled with more carbon dioxide if necessary to reach the desired pressure at the final reaction temperature.

The reactors were not placed in the aluminum block for the initial filling with carbon dioxide due to precautions involving the high temperatures. By starting with a lower pressure, the fittings on the reactors and tubing to the pressure gauge could be adjusted, if necessary, before working with these fittings near the hot aluminum block. Since these reactors were usually heated to temperatures greater than 200° C., the starting pressure of carbon dioxide at room temperature was estimated to give a desired final pressure at the high temperature.

Once the reactors were heated to the desired temperature and maintained at this temperature for a sufficient length of time to ensure that the maximum pressure had been attained, the pressure was noted and the pressure gauge was disconnected from the reactors. By disconnecting the pressure gauge and related tubing, the block could move freely from side to side without stressing any tubing that could create leaks in the reaction system. Agitation of the aluminum block was started after disconnecting the pressure gauge from the reactors.

After a specified reaction time the tube reactors were carefully removed from the aluminum block using leather gloves, and the reactors were immersed in an ice bath to quickly reduce the temperature. The reactors were kept in the ice bath for approximately ten minutes. The reactors were depressurized into a liquid solvent such as acetone or methanol, and analysis of the solids and liquid solvent were carried out by the indicated procedure.

4. Titanium Reactor

The titanium reactor equipment consists of a 100 ml reactor with four ports, an air-driven motor for turning the stirrer, a circulation bath, and a pump or pressure generator. The four ports on the reactor are used for the pressure gauge, thermocouple, carbon dioxide inlet, and a safety relief valve. The process of sealing the reactor takes at least 15 minutes to properly position the o-ring wrapped in TEFLON® (a trademark of E. I. du Pont de Nemours and Company, Wilmington, Del.) polytetrafluoroethylene, place the top housing with the stirrer and baffles onto the bottom part of the reactor, add the thermocouple to its port, and adjust the 6 bolts systematically to tighten the top housing to the bottom portion of the reactor. For heating or cooling, ethylene glycol was circulated through the reactor jacket using the circulation bath.

Starting material was weighed and added to the bottom portion of the reactor before bolting the top housing. For several runs, material was added in the glove box, but due to the size of the reactor parts and the ports, it was extremely difficult to transfer the reactor from the inner chamber to the outer chamber once it was together as one piece. Therefore, only a few runs with the titanium reactor were sealed in the glove box.

After sealing the reactor containing the starting materials, carbon dioxide was slowly added to the reactor to about 100 psi and then slowly released to purge air out of the system.

This purging process was repeated several times. Next cooling water was turned on to the top housing to keep the motor's bearings cool, and air was turned on to start the agitation. Carbon dioxide was incrementally added to the reactor as the circulation bath was used for temperature adjustment to the desired temperature set point. This is especially important when heating to high temperatures because if the reactor is filled with liquid carbon dioxide initially and then heated, the pressure will quickly increase towards the pressure limit of the reactor and some of the contents will have to be purged to reach the desired temperature, which results in a loss of starting material. In experiments for temperatures greater than 110° C., the circulation bath is used to attain that temperature and then the shell is left filled with ethylene glycol and heated further using heating tape. This procedure was used because there was no circulation bath or liquid pump available with the proper seals for such high temperatures. The reactor was depressurized into a liquid solvent such as acetone or methanol, and analysis of the solids and liquid solvent were carried out by the indicated procedure.

ANALYTICAL METHODS

In the Examples several analytical methods are referenced. These analytical methods are described below and are also numerically referenced in the individual examples.

All reagents were purchased from commercial suppliers. Product separation was accomplished using flash column chromatography with J. T. Baker silica gel (40 60 μm). Nuclear magnetic resonance (NMR) spectra were recorded on a Varian Gemini 300 MHz spectrometer, and high performance liquid chromatography (HPLC) was performed on a Hewlett Packard 1090 instrument.

Analysis Method #1

For this analysis column chromatography and NMR were used to determine the relative amounts of phenol, SA, and PHBA in the product The reactor was depressurized into acetone or methanol and the residue inside the reactor was removed using a spatula or by being dissolved in acetone or methanol and then removed with a pipette. A rotavap was used to remove the solvent from the reaction mixture. A small amount of methanol was added to the residue to make a solution for the column chromatograph. For the column, a solvent mixture of 50% petroleum ether and 50% ethyl ether was prepared as the eluent. The column was packed with silica gel, and the solution containing the reaction products was put on the top of the silica gel. The solvent mixture was then added to perform the liquid chromatograph. After the first fraction was collected, the eluent was changed to either pure ethyl ether or methanol to obtain the second fraction.

NMR spectra were taken for both fractions. The products and product distribution were determined based on the chemical shifts and peak area of each product. In cases where the yields were given, they were calculated based on the NMR spectra of the crude products.

Analysis Method #2

For this analysis column chromatography and NMR were used to determine the relative amounts of phenol, SA, and PHBA in the product.

The reactor was depressurized into acetone or methanol and the residue inside the reactor was removed using a spatula or by being dissolved in acetone or methanol and then removed with a pipette. A rotavap was used to remove the solvent from the reaction mixture. A small amount of methanol was added to the residue to make a solution for the column chromatograph. The column was packed with silica gel, and methanol was used as eluent. The methanol solution containing the reaction mixture was put on top of the silica gel, and then methanol was added to perform the liquid chromatograph. Only one fraction was collected. The solvent was removed and the residue was dried under vacuum pump.

The column fraction was analyzed using NMR. The distribution of the products was determined by the peak areas of the products from the NMR spectrum.

Analysis Method #3

For this analysis column chromatography and HPLC were used to determine the relative amounts of phenol, SA, and PHBA in the product.

The reactor was depressurized into acetone or methanol and the residue inside the reactor was removed using a spatula or by being dissolved in acetone or methanol and then removed with a pipette. A rotavap was used to remove the solvent from the reaction mixture. A small amount of HPLC grade methanol was added to the residue to make a solution for the column chromatograph. The column was packed with silica gel, and HPLC grade methanol was used as the eluent. The methanol solution of reaction mixture was put on top of the silica gel, and methanol was then added to perform the column chromatograph. Only one fraction was collected. This fraction was poured into a 500 ml volumetric flask, and a specified amount of an internal standard (2-naphthol) was added. HPLC grade methanol was then added to make a 500 ml solution.

HPLC was used for analysis. The HPLC separation conditions are shown in the following table. A calibration curve was obtained from standard solutions of phenol, PHBA and SA with 2-naphthol as an internal standard. The calibration curve was used to determine the yield and distribution of the products.

| HPLC Separation Conditions | |
|---|---|
| Solvent | 50% water + 35% tetrahydrofuran + 15% methanol |
| Flow rate | 1 ml/min |
| Injection Volume | 0.1 μl |
| Detector | Diode-array UV detector |

Analysis Method #4

For this analysis, a standard titration with NaOH was used to determine the relative amounts of phenol, SA, and PHBA in the product.

Analysis Method #5

For this analysis an ether/water treatment and NMR were used to determine the relative amounts of 2-naphthol and 6-HNA in the product.

After removal of the solvent from the reaction mixture, the crude product was obtained. The crude product was treated with a water and ether mixture. The ether layer was separated from the water layer. Then, the ether layer was washed with water, and the water layer was extracted with ether. All ether layers were combined and dried over $MgSO_4$. After removal of the ether, the residue was dried under a vacuum pump.

NMR was used to analyze the products.

In Examples 1–20 phenol was the hydroxyaromatic compound. In Examples 21–24, 2-naphthol was the hydroxy aromatic compound.

EXAMPLE 1

Using apparatus 4, 10.3 g of KF and 4.3 g phenol were added to apparatus 4. The reactor was pressurized to 114 bar with $CO_2$, the stirrer was set to 800 rpm, and heated at 120° C. for 86 h. Analysis by method 2 showed a yield of 10% PHBA and 5% SA.

EXAMPLES 2–7

These Examples are summarized in Table 3.

EXAMPLES 8–13

These Examples are summarized in Table 4. Also present in the reactor in Examples 8–10 was 4–5 ml of triglyme, and in Examples 11–13, 5–6 ml of tetraglyme were present.

EXAMPLES 14–15

These Examples were run using hexadecane as a "dispersant". To each reaction was added 41 ml of hexadecane. The results are summarized in Table 5.

EXAMPLES 16–20

These Examples were run using 4 ml of hexadecane as "dispersant". In Examples 17 and 18, 0.003 g of sodium stearate is also present, while in Examples 19 and 20 $10\mu$ of Tween®-80 was present. Results are summarized in Table 6.

EXAMPLES 21–24

In these Examples 2-napthol was the hydroxy aromatic compound. Results are summarized in Table 7.

TABLE 3

| Ex. No. | Ratio CsF:Phenol | Pressure (MPa) | Temperature (° C.) | Time (hr) | Apparatus | Discharge | Analytical Method | Results Yield | Ratio (p:o) |
|---|---|---|---|---|---|---|---|---|---|
| 2 | 2 | 54.5 | 160 | 22 | 1 | C | 1 | 40% | 0.9 |
| 3 | 2 | 44.7 | 160 | 5 | 1 | C | 2 | 62% | 2.0 |
| 4 | 2 | 27.3 | 160 | 6 | 2 | H | 2 | 72% | 1.2 |
| 5 | 2 | 35.7 | 160 | 1 | 1 | C | 2 | 59% | 2.9 |
| 6 | 2 | 36.7 | 130 | 20 | 1 | C | 2 | 69% | 3.6 |
| 7 | 2 | 37.0 | 100 | 1 | 1 | Q | 2 | Trace | |

Notes:
All reactors were loaded with starting material and sealed in the glove box. For discharge or depressurization C = room temperature discharge, H = discharge while reactor is still hot, Q = reactor quenched in ice water to cool within minutes and discharge at room temperature. All reactors were discharged into a solvent.

TABLE 4

| Ex. No. | Ratio CsF:Phenol | Pressure (MPa) | Temperature (° C.) | Time (hr) | Apparatus | Analytical Method | Results Yield | Ratio (p:o) |
|---|---|---|---|---|---|---|---|---|
| 8 | 2 | 36.6 | 130 | 1 | 1 | 4 | 16.0% | 5.0 |
| 9 | 2 | 24.0 | 130 | 1 | 1 | 1 | 27.0% | 9.0 |
| 10 | 2 | 53.0 | 130 | 2 | 1 | 1 | 25.0% | 3.0 |
| 11 | 2 | 66.0 | 130 | 1 | 1 | 1 | 26.0% | 4.0 |
| 12 | 4 | 44.1 | 130 | 1 | 1 | 1 | 44.0% | 5.0 |
| 13 | 8 | 32.9 | 130 | 1 | 1 | 1 | 45.0% | 5.0 |

Notes:
All reactors were loaded with starting material and sealed in the glove box.
All reactors quenched in ice water to cool within minutes for discharge at room temperature into a solvent.

TABLE 5

| Ex. No. | Ratio CsF:Phenol | Pressure (MPa) | Temperature (° C.) | Time (hr) | Apparatus | Analytical Method | Reactor Stir Rate | Results PHBA | SA |
|---|---|---|---|---|---|---|---|---|---|
| 14 | 2 | 11.9 | 130 | 17 | 4 | 3 | 700 | 12% | 44% |
| 15 | 2 | 10.3 | 110–125 | 17 | 4 | 3 | 650 | 16% | 5% |

Notes:
There were slow leaks and temperature probe adjustments during these runs
All reactors were loaded with starting material and sealed in the glove box with difficulty because of the size and geometry of the titanium reactor.
All reactors were cooled as quickly as possible (approximately 20–30 min) using the circulating bath and ice on the outside of the reactor. Depressurization took place at room temperature into a solvent.

TABLE 6

| Ex. No. | Ratio CsF:Phenol | Pressure (MPa) | Temperature (° C.) | Time (hr) | Apparatus | Analytical Method | Results Yield | Ratio (p:o) |
|---|---|---|---|---|---|---|---|---|
| 16 | 2 | 39.8 | 160 | 21 | 1 | 2 | 77.0% | 2.67 |
| 17 | 2 | 65.7 | 160 | 3 | 1 | 2 | 76.0% | 2.40 |
| 18 | 2 | 56.7 | 160 | 19 | 1 | 2 | 68.0% | 1.20 |
| 19 | 2 | 58.9 | 160 | 21 | 1 | 2 | 69.0% | 1.30 |
| 20 | 2 | 42.6 | 160 | 2 | 1 | 2 | 69.0% | 2.80 |

Notes:
All reactors were loaded with starting material and sealed in the glove box, except Example 16.
All reactors quenched in ice water to cool within minutes for discharge at room temperature into a solvent.

TABLE 7

| Run | Ratio CsF:N | Pressure (MPa) | Temperature (° C.) | Time (hr) | Apparatus | Analytical Method | Results |
|---|---|---|---|---|---|---|---|
| 21 | 4.7 | 11.9 | 250 | 16 | 3 | 5 | *Ratio = 1.8 |
| 22 | 4.7 | 13.7 | 250 | 23 | 3 | 5 | Ratio = 1.4 |
| 23 | 4.7 | 13.7 | 250 | 23 | 3 | 5 | Ratio = 0.6 |
| 24 | 0.5 | 10.4 | 250 | 2 | 3 | 5 | Trace of both isomers |

*Ratio = 6-hydroxy-2-naphthoic acid to 3-hydroxy-2-naphthoic acid
Notes: Examples were not loaded in the glovebox, and these reactors were quenched in ice water before depressurization at room temperature into a solvent.

What is claimed is:

1. A process for the production of aromatic hydroxycarboxylic acids, comprising, contacting, at a temperature of about 100° C. to about 300° C., an aromatic hydroxy compound and carbon dioxide in the presence of fluoride ion.

2. The process as recited in claim 1 wherein said carbon dioxide has a partial pressure of at least about 0.1 MPa.

3. The process as recited in claim 2 wherein the partial pressure is about 5 MPa to about 70 MPa.

4. The process as recited in claim 1 wherein said temperature is about 110° C. to about 250° C.

5. The process as recited in claim 3 wherein said temperature is about 110° C. to about 250° C.

6. The process as recited in claim 1 having a molar ratio of fluoride:aromatic hydroxy compound of at least about 1.

7. The process as recited in claim 1 having a molar ratio of fluoride:aromatic hydroxy compound of at least about 2.

8. The process as recited in claim 1 having a molar ratio of fluoride:aromatic hydroxy compound of about 4 to about 10.

9. The process as recited in claim 5 having a molar ratio of fluoride:aromatic hydroxy compound of at least about 2.

10. The process as recited in claim 1 wherein said aromatic hydroxy compound is phenol or 2-napthol.

11. The process as recited in claim 1 wherein said aromatic hydroxy compound is phenol.

12. The process as recited in claim 9 wherein said aromatic hydroxy compound is phenol.

13. The process as recited in claim 12 wherein said temperature is about 110° C. to about 160° C.

14. The process as recited in claim 1 wherein said fluoride is present as potassium fluoride, rubidium fluoride, or cesium fluoride.

15. The process as recited in claim 1 wherein said fluoride is present as cesium fluoride.

16. The process as recited in claim 9 wherein said fluoride is present as cesium fluoride.

17. The process as recited in claim 10 wherein said fluoride is present as cesium fluoride.

18. The process as recited in claim 1 wherein a dispersant is also present.

19. The process as recited in claim 18 wherein said dispersant is a polyether or a crown ether.

* * * * *